United States Patent [19]

Aries

[11] 3,989,828
[45] Nov. 2, 1976

[54] MIXED ESTERS OF ESTRADIOL AND ZERANOL

[76] Inventor: Robert Aries, 69, rue de la Faisanderie, 75116-Paris, France

[22] Filed: Aug. 9, 1974

[21] Appl. No.: 496,163

[30] Foreign Application Priority Data
Aug. 9, 1973   France .............................. 73.29133

[52] U.S. Cl. ............................ 424/240; 260/397.4; 260/397.5
[51] Int. Cl.² ........................................ A61K 31/56
[58] Field of Search ................. 424/240; 260/397.5, 260/397.4

[56] References Cited
UNITED STATES PATENTS
3,009,857  11/1961  Gassner .............................. 424/240
3,239,356  3/1966   Hodge et al. .................... 260/343.2
3,525,755  8/1970   Schalze ........................... 260/397.4

OTHER PUBLICATIONS
Chemical Abstracts, vol. 79, (1973), Pars. 105,458.

Primary Examiner—Elbert L. Roberts
Attorney, Agent, or Firm—Browdy and Neimark

[57] ABSTRACT

Mixed esters formed from a dicarboxylic acid and, on the one hand, estradiol or one of its monoesters and, on the other, zeranol or one of its mono or diesters; at least one of such mixed esters may be a constituent of a composition in implant form.

19 Claims, No Drawings

MIXED ESTERS OF ESTRADIOL AND ZERANOL

BACKGROUND OF THE INVENTION

The present invention relates to mixed esters formed from estradiol and zeranol on the one hand and a diacid on the other.

The significance of administering estradiol when rearing animals is already known, particularly through the action on the metabolism of calcium. However, this estradiol is rapidly degraded in the organism where it is free. Hence the interest of using it in the form of an ester whose hydrolysis is calculated in such a way that estradiol is only gradually released into the organism. Therefore the use of esters formed with alkanoic acids such as acetic, propionic and pyruvic acids (Leo, Belgian Pat. No. 646,319; Ciba, Swiss Pat. No. 380,118; Gyogyzeripari Kutato Intezet, Hungarian Pat. No. 150,957; Lakeside, Laboratory U.S. Pat. No. 2,623,886; Lovens Kemiske Fabrikved, U.S. Pat. No. 2,467,460; Organon Laboratories, U.S. Pat. No. 2,841,598; Dutch Pat. No. 81,258; and British Pat. Nos. 771,308 and 833,582; and Volovel Skii, Soviet Pat. No. 166,334) are recommended. Alkanoic esters with one or two halogens or a mercapto or dialkylamino group (Syntex Corporation, U.S. Pat. No. 3,275,623; Teikoku Japanese Pat. Nos. 4,967/60 and 21,179/61), benzoic esters (the above-cited Hungarian Pat. No. 150,957, Laboratoire Francais de Chimiotherapie, French Pat. No. 1,290,876 Merck A.G., British Pat. No. 1,022,422; Villax German Pat. No. 1,200,822) and phenylpropionic esters (Leo, German Pat. No. 1,123,666) are also recommended.

It is also known that zeranol has a rare anabolizing property for animals. This compound is trihydroxy-7,14,16-methyl-3-oxa-2-oxo-1-benzo-[c]-tetradecene-12a,16a of the following formula

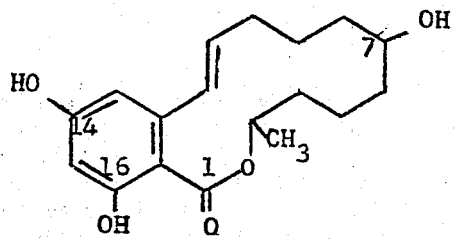

Its preparation and properties are described in U.S. Pat. Nos. 3,239,345, 3,239,348 and 2,196,019 of Commercial Solvents Corporation and in the corresponding French Pat. Nos. 6018M, 6612M, 6899M, 7807M and 1,481,985. When using this compound it is also important to select the esters in such a way that the duration of its effectiveness is increased. However, few esters of this compound are known and those which are known are light alkanoates described in U.S. Pat. No. 3,239,356 and French Pat. Nos. 6018M, 6899M, 7807M and 1,481,495 of Commercial Solvents Corporation.

The applicants have now discovered mixed esters formed from estradiol and zeranol whose anabolizing properties have proved to be remarkable. These esters are prepared from dicarboxylic acids.

BRIEF SUMMARY OF INVENTION

The object of the invention is therefore the new industrial products comprising mixed esters formed from a pharmaceutically acceptable dicarboxylic acid and, on the one hand, estradiol or one of its monoesters and, on the other, zeranol or one of its mono or diesters.

Estradiol is esterified with the diacid either in the 3-position or in the 17-position, whereby the position left free carries the hydroxy group or a group esterified by a carboxylic monoacid.

The monoacids which can esterify the free estradiol and/or zeranol groups are selected, for example, among the alkanoic, alkenoic, aralkanoic, aralkenoic, cyclanalkanoic and aroic acids. Such acids are, for example, formic, acetic, propionic, butyric, isobutyric, pivalic, valeric, isovaleric, caproic, isocaproic, heptanoic, caprylic, isocaprylic, pelargonic, capric, undecanoic, undecenoic, lauric, pyristic, palmitic, stearic, oleic, linoleic, lonoenic, margaric, arachidic, acetoxyacetic, propionoxyacetic, butoxyacetic, phenoxyacetic, chloroacetic, dichloroacetic, fluoroacetic, difluoroacetic, phenylacetic, diphenylacetic, methoxyacetic, ethoxyacetic, methylthioacetic, ethylthioacetic, methylsulphinylacetic, ethylsulphinylacetic, methylsulphonylacetic, ethylsulphonylacetic, propylsulphonylacetic, isopropylsulphonylacetic, cyclopentylsulphonylacetic, cyclohexylsulphonyl acetic, phenyl sulphonylacetic, phenoxyethylsulphonylacetic, (4-methoxyphenoxy)-2-ethylsulphonylacetic, benzoic, hexahydrobenzoic, 4-nitrophenylacetic, 4-acetamidophenylacetic, 4-trifluoroacetamidophenylacetic, phenylpropionic and nicotinic acids.

The invention also has for its object a process for the preparation of the said mixed esters according to which an activated derivative of the selected dicarboxylic acid is reacted with the estradiol or one of its monoesters, or on zeranol or one of its mono or diesters, then in a second stage the compound which has not yet been used is reacted with the activated carboxylic function which has remained free.

The activated derivatives are all those known to the skilled expert such as, for example, anhydrides, acid halides, mixed anhydrides formed by the action of a halogenoformic ester and derivatives formed by the action of a chloride of chlorocarbonyloxy or chlorosulphinyloxy-N,N-dimethylformiminium, the latter obtained as a result of the action of phosgene or thionyl chloride on N,N-dimethylformamide.

The mixed esters according to the invention having one or more hydroxy groups can be esterified with one of the above-mentioned mono acids.

Working preferably takes place in a solvent which is inert relative to the reagents present such as, for example, a hydrocarbon, an ether oxide, an oxidized heterocycle, a nitrile, a ketone, a halogenated hydrocarbon or a N,N-dialkylamide.

Working preferably takes place at a moderate temperature, for example, between −5° and +20° C, but it is sometimes advantageous to heat to complete the reaction.

It can be advantageous to use the O-metal derivative of the hydroxylated compound (estradiol or zeranol), such as, for example, halogenomagnesia, sodium or potassium derivatives. In other cases, an acid acceptor such as, for example, a tertiary nitrogenous base or an alkali metal carbonate is advantageously added to the reaction medium.

The suitable dicarboxylic acids are, for example, selected from the following:

Malonic, succinic, glutaric, adipic, pimelic, suberic, azelaic, sebacic, dimethyl-2,2-malonic, ethyl-2-methyl-2-malonic, ethyl-2-propyl-2-malonic, ethyl-2-butyl-2-malonic, ethyl-2-amyl-2-malonic, maleic, fumaric, glutaconic, muconic, 2,3-dihydromuconic, 2,5-dihydromuconic, 2-heptene-1,7-dioic, 3-heptene-1,7-dioic, 2,4-heptadiene-1,7-dioic, subercolic, glutamic, 2-hydroxyglutamic, aspartic, malic, tartronic, tartaric, phthalic, terephthalic, hexahydrophthalic and hexahydroterephthalic acids.

A further object of the invention are formulations in the form of granules, lozenges, pills or pellets containing at least one of the said mixed esters. The preferred forms are those permitting their introduction into animal tissues as long-duration implants. They are introduced by known means such as mechanical means, e.g., a cartridge for a trocar or with a gun provided with a storage means or bottle loaded with pellets.

The said formulations can optionally contain estradiol and/or zeranol in the free from or as esters not forming part of the invention. They can also contain a pharmaceutically acceptable solid excipient.

The solid excipients can be chosen from among the binding agents such as, for example, polyalkylene glycols, ethylenic or saturated fatty acids which optionally have a hydroxy group, ethylenic or saturated fat alcohols, cholesterol, lactose, ethyl cellulose, hydroxyethyl cellulose, propyl cellulose, metal stearates and natural or synthetic resins or rubbers and among inert charges such as, for example, talc and other non-toxic mineral powders.

The preferred polyalkylene glycols are selected from among the polyethylene glycols and polypropylene glycols having a molecular weight at least equal to 1000.

The preferred metal stearates are those of magnesium, aluminum and calcium.

Examples are given hereinafter with the sole object of illustrating the invention and without in any way limiting the same.

EXAMPLE 1

Mixed hexahydroterephthalic ester of 14-zeranol and 3-estradiol-17-propionate 32.8 g (0.1 mole) of estradiol-17-propionate and 10.1 g (0.1 mole) of triethylamine are introduced into 500 ml of anhydrous benzene. To this mixture are added 20.9 g (0.1 mole) of hexahydroterephthaloyl dichloride. Stirring is performed for 2 hours protected from air, then 32.2 g (0.1 mole) of zeranol and 10.1 g (0.1 mol) of triethylamine are added. Stirring is performed for 2 hours protected from air heated to 60° C and the mixture is filtered hot to eliminate the hydrochloride. The residue is washed twice with boiling benzene and the benzene solutions are combined in a rotary evaporator. The benzene is eliminated by distilling under a reduced pressure.

EXAMPLE 2

Mixed hexahydroterephthalic ester of 14-zeranol-16-benzoate and 3-estradiol-17-propionate 39.3 g (0.05 mole) of the mixed ester obtained in Example 1 and 5.1 g (0.05 mole) of triethylamine are introduced into 500 ml of anhydrous benzene. To this mixture are added 7.05 g (0.05 mole) of benzoyl chloride. Stirring is performed for 30 minutes, followed by refluxing for 2 hours. Hot filtration is carried out in order to eliminate the triethylamine hydrochloride and the residue is washed twice with boiling benzene. The benzene solutions are combined in a rotary evaporator and the benzene is eliminated by distilling under reduced pressure.

EXAMPLE 3

Mixed hexahydroterephthalic ester of 14-zeranol-16-benzoate-7-acetate and 3-estradiol-17-propionate 8.9 g (0.01 mole) of the mixed ester obtained in Example 2 are introduced into 100 ml of anhydrous pyridine. To this mixture are added 5 g of acetic anhydride. Refluxing is performed for 1 hour, then 90 ml are distilled under reduced pressure. The residue is poured into 100 ml of iced water and it is left at 0° C until the next day. The product formed is separated by eliminating the aqueous phase and is washed twice with cold water. Drying takes place in a ventilated oven at 40° C.

EXAMPLE 4

Mixed maleic ester of 16-zeranol-14-acetate and 17-estradiol-3-benzoate 37.65 g (0.1 mole) of estradiol-3-benzoate and 9.8 g (0.1 mole) of maleic anhydride are introduced into 500 ml of anhydrous pyridine. The mixture is progressively heated to reflux and reflux is maintained for 2 hours. 450 ml of pyridine are eliminated under reduced pressure in a rotary evaporator and the residue is poured into 500 ml of M/5 soda, cooled to 0° C. After stirring, the aqueous phase is eliminated and the product formed is introduced into 500 ml of benzene. The water present is eliminated by azeotropic distillation, followed by cooling to +5° C. 17 g (0.1 mole) of chlorocarbonyloxy-N-N-dimethylformiminium chloride in solution are added to 100 ml of benzene resulting from the action of the phosgene on N,N-dimethylformamide. Stirring is performed for 30 minutes protected from the air, followed by the addition of 36.4 g (0.1 mole) of zeranol-14-acetate and 10.1 g (0.1 mole) of triethylamine. The mixture is left protected from the air until the next day and is then heated to 75° C. Filtration takes place to eliminate the salts and the benzene is evaporated under reduced pressure.

EXAMPLE 5

Mixed maleic ester of 16-zeranol-7-benzoate-14-acetate and 17-estradiol-3-benzoate 41 g (0.05 mole) of the mixed ester obtained in Example 4 and 5.1 g (0.05 mole) of triethylamine are introduced into 500 ml of anhydrous dioxane. To this mixture are added 7.05 g (0.05 mole) of benzoyl chloride. The mixture is progressively heated to reflux and reflux is maintained for 30 minutes. Boiling filtration takes place to eliminate the triethylamine hydrochloride, then the dioxane are evaporated under reduced pressure. Washing is performed with a little pentane, followed by drying in a ventilated oven.

EXAMPLE 6

Mixed sebacic ester of 7-zeranol-14,16-diacetate and 3-estradiol 23.9 g (0.1 mole) of sebaccyl dichloride are introduced into 1 liter of anhydrous ethyl oxide. To this mixture are added 40.6 g (0.1 mole) of zeranol-14,16-diacetate and 10.1 g (0.1 mole) of triethylamine. The mixture is progressively heated to reflux which is maintained for 2 hours. Cooling takes place to +10° C. A solution of 27.2 g (0.1 mole) estradiol and 13.3 g (0.1 mole) of ethyl magnesium bromide containing 2 ml of pyridine in 3 l of anhydrous ethyl oxide is added. The mixture is left for 24 hours at ambient temperature and is then refluxed for 5 hours. This is followed by cooling, washing with a saturated aqueous solution of sodium bicarbonate and then with pure water. Drying takes place on calcium sulphate and then the ethyl oxide is evaporated.

EXAMPLE 7

Formulations for implants (values in mg)

| | A | B | C | D | E | F | G | H |
|---|---|---|---|---|---|---|---|---|
| Mixed salt of Example 1 | 50 | 25 | — | — | — | — | — | — |
| Mixed salt of Example 2 | — | — | 60 | 60 | 30 | — | — | — |
| Mixed salt of Example 3 | — | — | — | — | — | 65 | 40 | — |
| Mixed salt of Example 6 | — | — | — | — | — | — | — | 45 |
| Estradiol | — | 10 | — | — | — | — | 7 | — |
| Estradiol-3-benzoate | — | — | — | — | 15 | — | — | — |
| Zeranol | 120 | — | — | 60 | 70 | 120 | 100 | 40 |
| Zeranol-14,16-diacetate | — | 140 | — | 70 | 70 | — | — | 90 |
| Polyethylene glycol (mol. wt. 6000) | 35 | — | 12 | — | — | — | — | 35 |
| Polyethylene glycol (mol. wt. 4000) | — | — | — | — | 10 | 40 | — | — |
| Magnesium stearate | 5 | 4 | 2 | 3 | 8 | 6 | 1 | 5 |
| Talc | — | — | — | 3 | — | — | 2 | — |
| Cholesterol | — | — | — | 15 | — | — | 10 | — |
| Ethyl cellulose | — | — | — | 10 | 15 | — | 1 | — |
| Palmitic acid | — | 36 | — | — | — | — | — | — |

What is claimed is:

1. A mixed ester formed from a pharmaceutically acceptable dicarboxylic acid selected from the group consisting of malonic, succinic, glutaric, adipic, pimelic, suberic, azelaic, sebacic, dimethyl-2,2-malonic, ethyl-2-methyl-2-malonic, ethyl-2-propyl-2-malonic, ethyl-2-butyl-2-malonic, ethyl-2-amyl-2-malonic, maleic, fumaric, glutaconic, muconic, 2,3-dihydromuconic, 2,5-dihydromuconic, 2-heptene-1,7-dioic, 3-heptene-1,7-dioic, 2,4-heptadiene-1,7-dioic, subercolic, glutamic, 2-hydroxyglutamic, aspartic, malic, tartronic, tartaric, phthalic, terephthalic, hexahydrophthalic and hexahydroterephthalic acids esterified with both estradiol or a monoester thereof and zeranol or a mono- or diester thereof, said mono- or diesters of estradiol and zeranol being with a monocarboxylic acid or acids selected from the group consisting of the following acids: formic, acetic, propionic, butyric, isobutyric, pivalic, valeric, isovaleric, caproic, isocaproic, heptanoic, caprylic, isocaprylic, pelargonic, capric, undecanoic, undecenoic, lauric, pyristic, palmitic, stearic, oleic, linoleic, lonoenic, margaric, arachidic, acetoxy-acetic, propionoxyacetic, butoxyacetic, phenoxyacetic, chloroacetic, dichloroacetic, fluoroacetic, difluoroacetic, phenylacetic, diphenylacetic, methoxyacetic, ethoxyacetic, methylthioacetic, ethylthioacetic, methylsulphinylacetic, ethylsulphinylacetic, methylsulphonylacetic, ethylsulphonylacetic, propylsulphonylacetic, isopropylsulphonylacetic, cyclopentylsulphonylacetic, cyclohexylsulphonylacetic, phenylsulphonylacetic, phenoxyethylsulphonylacetic, (4-methoxyphenoxy)-2-ethylsulphonylacetic, benzoic, hexahydrobenzoic, 4-nitrophenylacetic, 4-acetamidophenylacetic, 4-trifluoroacetamidophenylacetic, phenylpropionic and nicotinic acids.

2. A mixed ester according to claim 1, in which the estradiol is also esterified with one of said monocarboxylic acid.

3. A mixed ester according to claim 1, in which the zeranol is also esterified with one or two of said monocarboxylic acids.

4. A process for the preparation of the mixed esters according to claim 1, in which an activated derivative of said selected dicarboxylic acid is reacted with estradiol or one of its said monoesters, or with zeranol or one of its said mono or diesters, then in a second stage the compound which still has not been used is reacted with the activated carboxylic function which has remained free.

5. A process according to claim 4, in which the activated derivative is an acid halide or an anhydride.

6. A process according to claim 4, in which the activated derivative is formed by the action of a halogenoformic ester on the considered carboxylic group or groups.

7. A process according to claim 4, in which the activated derivative is formed by the action of chlorosulphinyloxy-N,N-dimethyl formiminium or chlorocarbonyloxy chloride on the considered carboxylic groups.

8. A process according to claim 4, in which the reaction medium contains an acid acceptor selected from among the tertiary nitrogenous organic or mineral bases.

9. A process according to claim 8, in which the acid acceptor is triethylamine.

10. A process according to claim 4, in which the zeranol and/or estradiol are used in the form of their O-metal derivatives.

11. A process according to claim 10, in which the O-metal derivatives are halogenomagnesia derivatives.

12. A composition containing at least one of the mixed esters according to claim 1 in an amount sufficient to promote anabolism in animals, and a solid excipient and a free active compound selected from the group consisting of estradiol, zeranol and their pharmaceutically acceptable esters other than those of claim 1, wherein said mixed ester is present from 12 – 81% by weight, said estradiol or ester thereof is present up to 77% by weight, said zeranol or ester is present up to 65% by weight, the remainder being constituted by said solid excipient.

13. A composition according to claim 12, in which the excipients are selected from among the binding agents and inert charges.

14. A composition according to claim 13, in which the binding agents are selected from among the polyalkylene glycols, ethylenic or saturated fatty acids which optionally have a hydroxy group, ethylenic or saturated fat alcohols, cholesterol, lactose, ethyl cellulose, hydroxyethyl cellulose, propyl cellulose, metal stearates and natural or synthetic resins or rubbers.

15. A composition according to claim 14, in which the binding agents are selected from among the polyethylene glycols and polypropylene glycols having a molecular weight at least equal to 1000.

16. A product according to claim 1 in which the product is formulated in the form of granules, lozenges, pills or pellets.

17. A composition in accordance with claim 12 in which the composition is formulated in the form of granules, lozenges, pills or pellets.

18. A composition containing at least one of the mixed esters according to claim 1 in an amount sufficient to promote anabolism in animals and a free active compound selected from the group consisting of estradiol, zeranol and their pharmaceutically acceptable esters other than those of claim 1, wherein said mixed ester is present from 12 – 81% by weight, said estradiol or ester thereof is present up to 77% by weight and said zeranol or ester is present up to 65% by weight.

19. A composition in accordance with claim 18 in which the composition is formulated in the form of granules, lozenges, pills or pellets.

* * * * *